US011229755B2

(12) United States Patent
Ott et al.

(10) Patent No.: US 11,229,755 B2
(45) Date of Patent: Jan. 25, 2022

(54) HYDRATION SYSTEM (71) Applicant: LEXION MEDICAL, LLC, St. Paul, MN (US)

(72) Inventors: Douglas E. Ott, Macon, GA (US); Nathanial Tran, Lakeville, MN (US)

(73) Assignee: LEXION MEDICAL, LLC, St. Paul, MN (US)

( * ) Notice: Subject to any disclaimer, the term of this patent is extended or adjusted under 35 U.S.C. 154(b) by 0 days.

(21) Appl. No.: 15/330,741

(22) Filed: Nov. 1, 2016

(65) Prior Publication Data

US 2017/0049975 A1 Feb. 23, 2017

Related U.S. Application Data

(63) Continuation of application No. 13/815,300, filed on Feb. 19, 2013, now Pat. No. 9,533,110, which is a continuation-in-part of application No. 13/507,733, filed on Jul. 24, 2012, now Pat. No. 8,836,521, which is a continuation of application No. 12/288,133, filed on Oct. 16, 2008, now Pat. No. 8,269,638, said application No. 13/815,300 is a continuation-in-part (Continued)

(51) Int. Cl.
*A61M 13/00* (2006.01)
*A61M 16/10* (2006.01)
*A61M 16/16* (2006.01)
*A61M 16/00* (2006.01)

(52) U.S. Cl.
CPC ...... *A61M 13/003* (2013.01); *A61M 16/0051* (2013.01); *A61M 16/024* (2017.08); *A61M 16/109* (2014.02); *A61M 16/161* (2014.02); *A61M 16/107* (2014.02); *A61M 16/16* (2013.01); *A61M 2205/18* (2013.01); *A61M 2205/3331* (2013.01); *A61M 2205/3334* (2013.01); *A61M 2205/3368* (2013.01); *A61M 2205/3379* (2013.01); *A61M 2205/36* (2013.01); *A61M 2205/3653* (2013.01); *A61M 2205/50* (2013.01); *A61M 2205/75* (2013.01)

(58) Field of Classification Search
CPC ...... A61M 2202/0468; A61M 2202/02; A61M 13/003; A61M 2205/3334; A61M 2205/3331; A61M 2205/3368; A61M 2205/3379; A61M 2205/3653; A61M 16/109; A61M 16/161; A61M 16/0051; A61M 2205/36; A61M 16/024; A61M 16/107; A61M 16/16; A61M 2205/18; A61M 2250/50; A61M 2250/75
USPC .......................................................... 604/26
See application file for complete search history.

(56) References Cited

U.S. PATENT DOCUMENTS

| 6,689,095 B1 * | 2/2004 | Garitano ........... A61M 37/0076 604/70 |
| 2004/0254524 A1 * | 12/2004 | Spearman ........... A61M 13/003 604/26 |

(Continued)

*Primary Examiner* — Tiffany Legette
(74) *Attorney, Agent, or Firm* — Johnson & Phung LLC (57) ABSTRACT

A medical gas condition system for supplying a liquid hydration fluid to a hydrator before or during an ongoing medical procedure by coupling the flow of liquid hydration fluid into the hydrator to either the absence of flow of medical insufflation gas into the hydrator or to a condition where the liquid hydration fluid can be absorbed by a hydrator without being forced through the hydrator in liquid form.

8 Claims, 3 Drawing Sheets

Related U.S. Application Data of application No. 13/573,861, filed on Oct. 9, 2012, now Pat. No. 10,076,612.

(60) Provisional application No. 61/062,064, filed on Jan. 23, 2008, provisional application No. 61/627,537, filed on Oct. 13, 2011.

(56) References Cited

U.S. PATENT DOCUMENTS

| | | | |
|---|---|---|---|
| 2005/0107766 A1* | 5/2005 | Ott | A61M 13/003 604/500 |
| 2006/0058731 A1* | 3/2006 | Burnett | A61M 1/1678 604/29 |
| 2006/0270971 A1* | 11/2006 | Gelfand | A61B 5/201 604/66 |
| 2007/0060874 A1* | 3/2007 | Nesbitt | A61M 5/14228 604/80 |
| 2009/0184832 A1* | 7/2009 | Lloyd | A61M 13/003 340/635 |
| 2009/0240192 A1* | 9/2009 | Power | A61B 17/3474 604/26 |
| 2010/0241061 A1* | 9/2010 | Ott | A61B 17/3474 604/26 |

\* cited by examiner

HYDRATION SYSTEM

CROSS REFERENCE TO RELATED APPLICATIONS

This application is a continuation of application Ser. No. 13/815,300 filed Feb. 19, 2013 titled HYDRATION SYSTEM, which is a continuation-in-part of application Ser. No. 13/507,733, filed on Jul. 24, 2012 titled HYDRATION ALERT (now U.S. Pat. No. 8,836,521), which is a continuation of application Ser. No. 12/288,133 filed Oct. 16, 2008 titled HYDRATION ALERT (now U.S. Pat. No. 8,269,638), which claims benefit from provisional application 61/062,064 filed Jan. 23, 2008 titled HYDRATION ALERT; and application Ser. No. 13/815,300 filed Feb. 19, 2013 is a continuation-in-part of application Ser. No. 13/573,861 filed Oct. 9, 2012 titled GAS CONDITIONING DEVICES, which claims benefit from provisional application 61/627,537 filed Oct. 13, 2011 titled GAS CONDITIONING DEVICES

FIELD OF THE INVENTION

This invention relates generally to medical procedures and, more specifically, to apparatus and method for charging a hydrator in a medical insufflation apparatus.

STATEMENT REGARDING FEDERALLY SPONSORED RESEARCH OR DEVELOPMENT

None

REFERENCE TO A MICROFICHE APPENDIX

None

BACKGROUND OF THE INVENTION

The concept of medical apparatus for insufflating a gas during surgery is described in Douglass et al. U.S. Pat. Nos. 5,411,474; 6,068,609 and 7,066,902. Briefly, an insufflation gas is heated and hydrated before the gas is directed into a body cavity through a device such as a trocar. In order to hydrate the insufflation gas a charge of hydration fluid is typically injected into a chamber where the hydration fluid can humidify the insufflation gas before the insufflation gas is injected into a body cavity of a patient. Typically, a charge of hydration fluid is injected into a heater hydrator to humidify the insufflation gas as it travels through a chamber in the heater hydrator. When the charge of hydration fluid injected into the heater hydrator is spent or runs low, then a fresh charge may be introduced into the heater hydrator.

Inflating a patient's body cavity with a medical insufflation gas distends, or inflates, the body cavity producing an operating region within the body cavity, which enables performance of a minimally invasive surgical procedure on the patient. Douglas Ott et al. U.S. Pat. Nos. 5,411,474; 6,068,609 and 7,066,902 show and describe a medical apparatus that humidifies or otherwise conditions an insufflation gas during such a surgical procedure. Briefly, the patents describe the heating and hydrating of the insufflation gas, i.e. the conditioning of the insufflation gas, before injecting the insufflation gas into a body cavity through an inflation device such as a trocar. In order to hydrate the insufflation gas one injects a charge of hydration fluid into a hydrator where the hydration fluid contacts the insufflation gas and humidifies the insufflation gas before injecting the insufflation gas into the patient's body cavity. In addition, one may heat the insufflation gas thereby bringing the insufflation gas to the proper temperature for insertion into the body cavity. During the medical procedure one periodically injects the conditioned insufflation gas into the patient's body cavity through an inflation device such as trocar in order to maintain the body cavity in an inflated condition since some of the insufflation gases escape from the body cavity during the performance of the surgical procedure.

Laparoscopy is an example of one type of a minimal invasive surgery where one inflates a body cavity with a medical insufflation gas. In a laparoscopic surgical procedure, a surgeon manipulates instruments inside a patient's inflated body cavity through a trocar. The most prevalent medical insufflation gas used in the laparoscopic surgical procedures is carbon dioxide, which is directed into a peritoneal cavity through a trocar. A device called an insufflator regulates the delivery of the carbon dioxide gas to the body cavity. Typically, the insufflator receives an unconditioned medical gas from a gas canister containing a medical grade insufflation gas with the gas typically having water vapor concentrations on the order of 200 parts per million, which is extremely dry. In addition to the insufflation gas being dry, the unconditioned insufflation gas delivered from the gas canister is generally at a temperature less than the ambient temperature. In a typical surgical setting the ambient temperature level of the surgical setting may be about 20° C. and the patient's normal body temperature of 37° C., which results in a large temperature difference between the temperature of the unconditioned insufflation gas and the body temperature of the patient. Studies performed over several decades have produced a large body of evidence that shows that the use of unconditioned insufflation gas, such as carbon dioxide, in laparoscopic surgical procedure results in adverse effects for the patient. However, by conditioning the insufflation gas, with respect to both its temperature and relative humidity, reveals that one can avoid the adverse effects that occur with unconditioned insufflation gas.

As it was assumed that conditioning of the insufflation gas did not provide a physiological benefit to the patient the early medical devices transporting the insufflation gas from the insufflator to the patient consisted of a length of plastic tubing with an inline filter attached to the tubing to block unwanted contaminates from the source of the insufflation gas. Since no conditioning was performed to the insufflation gas the body cavity of the patients was inflated with a cold dry gas. The insufflation systems have evolved to the current state where an insufflation devices can both warm and humidify an insufflation gas such as carbon dioxide gas although other insufflation gases may also be warmed and humidified. Such insufflation systems may increase the moisture content of the gas to near 100% relative humidity. Such gas conditioning systems, which are shown in U.S. Pat. Nos. 5,411,474 and 6,068,609, have resulted in physiological benefits to the patient.

The benefits of insufflation systems, which conditions the insufflation gas, reveal that certain operational requirements of the insufflation system may require disruptions of the medical procedure or at least cause inconveniences. For example, the medical personal may need to separately introduce the hydration fluid into a hydrator in order to hydrate the insufflation gas before the surgical inflation gas flows into the patient's body cavity. Typically, the hydration fluid needs to be introduced into the hydrator before the surgical procedure begins and periodically during the surgical procedure. For example, after an initial hydration of the hydrator, one may add hydration fluid to the hydrator after a threshold condition such as 150 liters of insufflation gas have passed through the hydrator with the threshold condition based on a determination that shows the hydrator can hold sufficient hydration fluid to hydrate at least 150 liters. While the task of periodically supplying hydration fluid to the hydrator does not present an onerous task for medical personnel it has the potential to be accidentally overlooked during the surgical procedure resulting in unhydrated insufflation gas being supplied to the patient. Therefore an apparatus and method that can automatically supply a hydration fluid into the existing hydrators, which may be done on-the-go, would provide a benefit to the medical staff and the patient. Another inconvenience with the existing hydration systems is that, the supply of medical gas to the hydrator needs to be suspended or shut off when supplying the hydration fluid to the hydrator in order to prevent the hydration fluid from being forced through the hydrator and into the patient's body cavity without having an opportunity to being absorbed by the hydration member in the hydrator. The failure of the hydrator to absorb the hydration fluid may have adverse effects including accumulation of fluid on the lens of a visualization device, which is used to during the medical procedure, thereby obstructing the surgeons view of the surgical site.

SUMMARY OF THE INVENTION

The present invention provides an alert system that may generate an alert to recharge hydration fluid in a humidifier when such a recharge is desirable such as when a charge of hydrated fluid used to hydrate insufflation gas is running low or has been consumed.

One aspect of the invention is an apparatus including an alarm for alerting an operator to recharge a humidifier, wherein such alarm is generated other than through the use of a humidity sensor. In one embodiment the total work $W_T$. (which can be calculated by integrating a function of power versus time)) performed during heating and hydrating an insufflation gas is measured to provide an alert signal. The alert signal can activate an alarm when the total work performed is more than a particular threshold. In another embodiment, a flow meter or a mass meter is used to measure the total flow of insufflation gas so that when the total flow of insufflation gas reaches a predetermined level an alarm is activated.

The invention has several important technical advantages. Embodiments of the invention may have none, some, or all of these advantages. The invention may allow more accurate determination of when a humidifier should be recharged than is possible with a humidity sensor. Because humidifiers used in medical procedures may be disposable, the methods disclosed in the present invention may be superior from a cost and waste standpoint as reusable components can be used to sense the need for recharge instead of using a disposable humidity sensor. The invention may allow multiple methods to be used simultaneously to create a signal that a humidifier should be recharged with humidifying liquid, thus providing a way to verify recharge is desirable.

The invention comprises both a sensing and a method and an apparatus for supplying liquid hydration fluid to a hydrator in a medical gas conditioning system either before or during a medical procedure with the system that may include a sensor for determining a flow condition of the insufflation gas and a controller for initiating the injection of the liquid hydration fluid into a hydrator during flow conditions where the liquid hydration fluid can be absorbed by the hydration media in the hydration chamber to prevent the insufflation gas from carrying the liquid hydration fluid through the insufflator. The supplying of liquid hydration fluid may be based on time intervals where there is an absence of insufflation gas flowing into the hydrator thus enabling the liquid hydration fluid to be absorbed by the hydrator without the insufflation gas accidentally forcing the liquid hydration fluid through the hydrator.

A feature of the invention is that the liquid hydration fluid may also be supplied during a flow of insufflation gas into a hydrator if the flow of insufflation gas is below a critical condition.

A feature of the system is that the liquid hydration fluid may be automatically supplied to the hydrator prior during a medical procedure without the need to monitor the amount of liquid hydration fluid in the hydrator.

Further features of the inventions are that the time periods for supplying of hydration fluid may be limited to occur only after a threshold condition has occurred such as after an initial volume of insufflation gas has been delivered to the hydrator.

The invention has several important technical advantages. Embodiments of the invention may have none, some, or all of these advantages. The invention may allow more accurate determination of when a humidifier should be recharged than is possible with a humidity sensor. Because humidifiers used in medical procedures may be disposable, the methods disclosed in the present invention may be superior from a cost and waste standpoint as reusable components can be used to sense the need for recharge instead of using a disposable humidity sensor. The invention may allow multiple methods to be used simultaneously to create a signal that a humidifier should be recharged with humidifying liquid, thus providing a way to verify recharge is desirable.

DESCRIPTION OF THE PREFERRED EMBODIMENT

Figure 1:
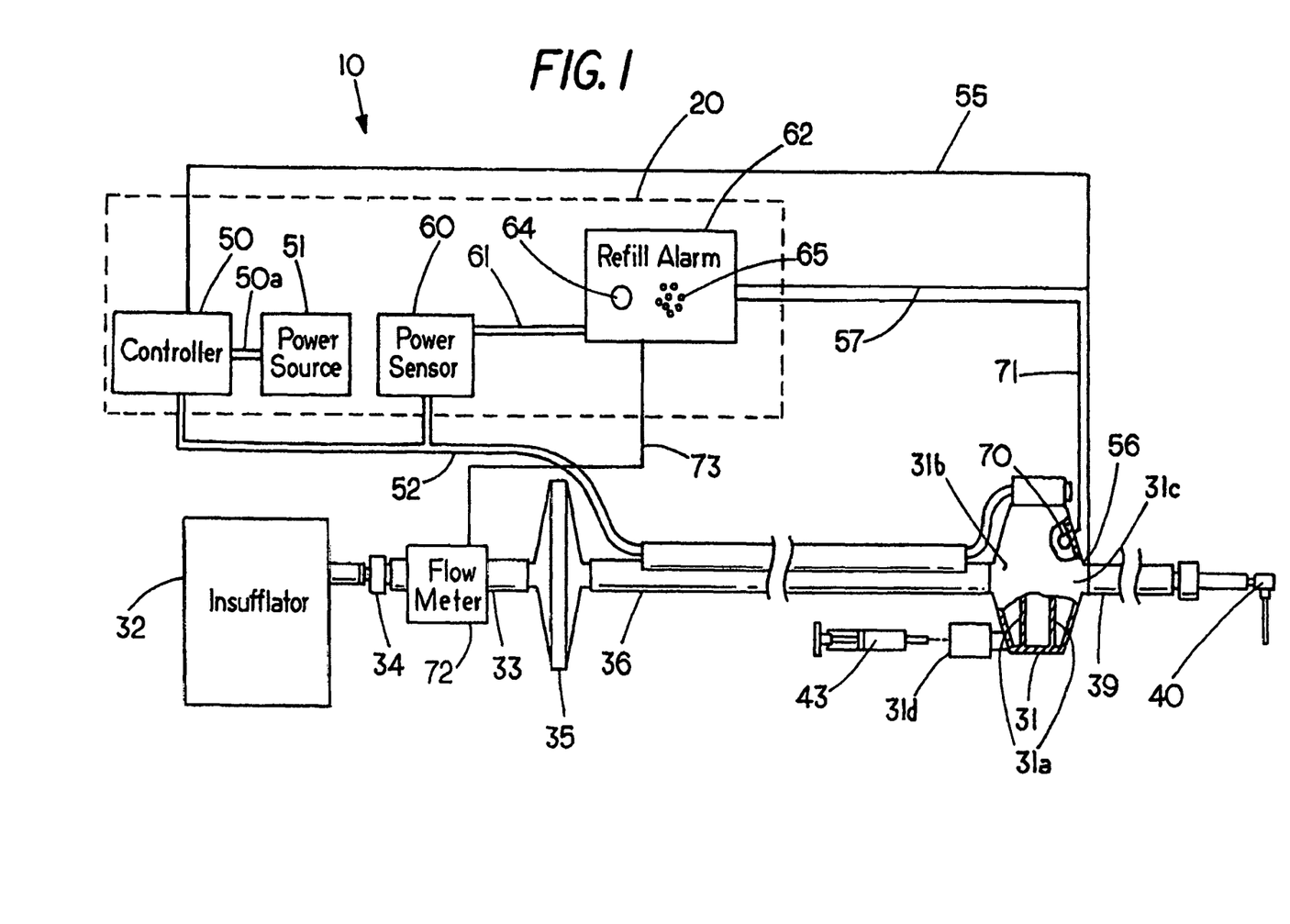
FIG. 1 is a schematic view of one embodiment of a refill system in conjunction with an apparatus for conditioning an insufflation gas.

FIG. 1 shows an apparatus 10 for maintaining conditioning of an insufflation gas during a medical procedure. Typically, the medical procedure is endoscopy and more specifically laparoscopy. The invention may also be used during thoracoscopy. The system may include a heater hydrator 31 for heating and hydrating an insufflation gas delivered from an insufflator 32 that supplies an insufflation gas to the heater hydrator as needed. In some embodiments, heater hydrator 31 may be replaced by a hydrator alone. Insufflator 32 is a laparoscopic insufflator in this embodiment.

Located within (or surrounding) heater hydrator 31 is an electrical heater 31a for heating an insufflation gas to a temperature within a desired temperature range, which typically is about 34-38.degree.C. The insufflator 32 connects (typically indirectly) to heater hydrator 31 through, for example, a coupling 34, a flow meter 72, tubing 33 a filter 35 for removing impurities and a tubing 36 that is secured to an inlet 31b of heater hydrator 31. An outlet 31c on heater hydrator 31 may connect to tubing 39 that connects to a trocar 40 (or verres needle) for delivery of the conditioned insufflation gas to a body cavity of a patient during a medical procedure. Thus the insufflator 32 regulates the flow of insufflation gas, which is usually located in the operating room. Systems for delivery of insufflation gas are shown in Ott et al. U.S. Pat. No. 6,068,609, which is hereby incorporated by reference. Note that in some embodiments the heater may be in tubing leading to the patient (e.g. between an insufflator and a trocar or verres needle). Some or all of these components may be omitted or rearranged without departing from the scope of the invention. For example, flow meter 72 may be omitted if the flow meter is not being used to sense when recharge is desirable. Flow meter 72 may also be a part of insufflator 32. Insufflator 32 may also have one or more flow meters in addition to flow meter 72. Flow meter 72 may be placed at any point between insufflator 32 and a patient. In some embodiments, filter 35 may be omitted or located in a different place along the flow channel. Ideally, tubing 39 is less than 24 inches long, more ideally less than 15 inches long, more ideally less than 10 inches long, and more ideally less than 6 inches long. Other lengths of tubing 39 may be used without departing from the scope of the invention. In addition, tubing could be placed between coupling 34 on insufflator 32 and flow meter 72. These are only a few examples of how components could be rearranged, added, or omitted, without departing from the scope of the invention.

In operation of system 10 a valve (not shown) on a trocar 40 or the like is opened to allow the insufflation gas to flow from insufflator 32 through coupling 34, a flow meter 72, tubing 33, a filter 35 and tubing 36 whereupon it enters heater hydrator 31. A controller 50, which connects to power source 51 through electrical lead 50a, may comprise, for example, a microcontroller or other electric circuitry to regulate the power delivered to heater 31a from a power source 51. The insufflation gas enters the heater hydrator 31 and is heated by the heater 31a to a temperature within a desired temperature range. In a preferred embodiment the controller 50 comprises a microcontroller with pulse-width modulation outputs. A conventional power mosfet can be connected to the microcontroller pulse-width modulation outputs to turn the power on and off to the heater 31a. Analog circuits may also be used to control power such as are described in U.S. Pat. No. 5,411,474. As will be discussed further below, controller 50 may be external to or internal to Insufflator 32.

In addition to heating the insufflation gas to the proper body entry temperature in embodiments where gas is heated, the insufflating gas may also be hydrated by the presence of a charge of hydration fluid in heater hydrator 31. Humidification may occur in any manner such as by gas flowing through and/or over the hydration fluid or by flowing through and/or over an absorbent material that has absorbed some or all of the hydration fluid.

Because hydration fluid is consumed during an operation, it is desirable to replenish it from time to time during at least some operations. The insufflation gas is typically supplied from a pressurized cylinder of insufflation gas (not shown) within or connected to insufflator 32. A supply of gas from another source such as one might find supplied from the wall of an operating room from a centralized supply may also be used. As gas leaks out or is deliberately released from a patient's abdomen during a laparoscopic procedure, insufflator 32 may control the flow of gas such that the released gas is replenished. Insufflator 32 may also provide flow control to control the maximum flow rate of gas from the insufflator to the patient and pressure control to control the maximum pressure at which insufflator 32 provides gas to the patient. In most insufflators 32, the maximum pressure and flow rate are adjustable by the user of the apparatus. Depending upon the amount of gas consumed during a surgical procedure, the humidifier may or may not require recharging with humidifying liquid.

In operation of the system 10 the insufflation gas is hydrated by the consumption of hydration fluid in the heater hydrator 31. Hydration fluid may be supplied to heater hydrator 31 by various means. In the embodiment shown one can use a syringe 43 to manually inject a charge of hydration fluid into the heater hydrator 31 through a charging port 31d. One can charge or recharge (or both) heater hydrator 31 in this manner. Other modes could include automatic injecting of a hydration fluid into the heater hydrator through a dedicated hydration fluid supply line connected to heater hydrator 31. Whatever method is used, a quantity (which quantity may be known approximately) of hydration fluid may be introduced in some manner into the heater hydrator, which is designated herein as a charge of hydration fluid. While the hydration fluid is injected into the heater hydrator 31 through a charging port 31d in this embodiment, other methods of replenishing the hydration fluid can be used. For example, fluid could be introduced through the gas inlet or outlet of heater hydrator 31.

Hydration fluid can be any desirable hydration fluid such as, for example, water, saline solution, or distilled water. In other embodiments, hydration fluid may include a drug such as an anesthetic, antibiotic, etc.

In various embodiments of the invention, the user is alerted as to when to recharge the heater hydrator 31 through the use of a refill alarm system 20, shown in FIG. 1 in dashed lines. To heat the insufflation gas, a power source 51 may supply power through electrical leads 52 to the heater 31a. The heater may heat both the insufflation gas and the hydration fluid to be within a desirable temperature range for provision of the heated and humidified insufflation gas into a body cavity. In the embodiment shown, a temperature sensor 56 within the heater hydrator 31 connects to controller 50 through wire lead 55 for use in determining whether the heated and humidified gas is within the proper temperature range. The microcontroller in controller 50 (or suitable analog circuitry) may turn on (or pulse) the mosfet in controller 50 allowing the power source 51 to supply power to the heater 31a through electrical leads 52. Other methods of power control can also be used without departing from the scope of the invention. Thus, the insulating gas can be maintained within the proper temperature range through the use of heater 31a, temperature sensor 56 and controller 50.

In some embodiments, multiple temperature sensors 56 may be used. For example, two temperature sensors could be used and a malfunction detected if their measured temperature varied more than a predetermined amount. In some embodiments, heater hydrator 31 will have a fixed temperature range that is not adjustable. In other embodiments, controls may be provided to adjust the temperature range. Also, temperature sensor 56 may be placed anywhere within heater hydrator 31 or external to heater hydrator 31. More responsive temperature control can normally be obtained if temperature sensor 56 is sensing a temperature equal to or proportional to the temperature of the gas after it has been heated and humidified. Also, temperature sensor 56 could be located in tubing 39 or in trocar 40.

Work done by the heater 31a to maintain the insulation gas in a hydrated condition within a desirable temperature range may be proportional to the quantity of hydration fluid consumed. By measuring the work performed by the heater 31a during the heating and hydration process, one can determine when it may be desirable to replenish the hydration fluid. One can measure the work performed when heating and hydrating an insufflation gas when using a full charge or near full charge of hydration fluid. In other words, one can charge the device and then heat and hydrate a sufficient quantity of gas to deplete (either completely or substantially) the hydration fluid. One can experimentally determine the work performed in depleting the hydration fluid. By such measurement, one can obtain a total work level $W_T$. Once the total work level $W_T$ is known, one can then experimentally determine a recharge work level $W_C$, which is equal to or less than the total work $W_T$, to use for activating the alarm to alert a person to recharge the heater hydrator 31. For example, one can select a work amount of 0.9 $W_T$ as a work level where an alarm is sounded to indicate that the heater hydrator 31 should be recharged.

Work can be measured by making a series of power measurements using power sensors or current and voltage sensors. In some embodiments, a power meter may be used to make a series of power measurements. Where a microcontroller is used, the voltage supplied to the heater may be known and a current sensor may be used to measure the current that is then multiplied by the known voltage to determine instantaneous power. Work can be calculated by determining the area under a graph of power versus time. Most often, some type of numerical method will be used to calculate work such as, for example, (a) assuming a power measurement is constant for a particular amount of time, or (b) by using some type of interpolation using multiple power measurements. Thus, a series of power measurements can be made and the total work performed during a period of time calculated using the power measurements and time. For purposes of this application, any calculation that approximates work will be considered to be a measurement of work. The accuracy of a particular recharge signal may depend upon the accuracy of the measurement of work (both during operation of the device and in the initial experiments to determine the total work performed while a charge is evaporating).

The time of consumption of a charge of hydration fluid cannot be reliably predicted because the amount of insufflation gas consumed and hence the amount of hydration fluid consumed during a particular time period can vary greatly depending upon the surgical procedure. However, when sufficient hydration fluid has been consumed that the gas is not reaching approximate saturation, the power consumption of the heater hydrator 31 will decline because less heat is consumed by the humidification process. By measuring the total work performed, one can indirectly determine that the humidity of the humidified gas is declining. The invention thus advantageously allows recharging of the hydration fluid in many instances before complete consumption of the hydration fluid has occurred.

In order to perform the power measurements described above, controller 50 may include an internal power sensor in the microcontroller (or other analog circuitry to sense power) or an external power sensor 60. Controller 50 (or suitable analog or digital circuitry) may be programmed with the work levels $W_T$ and $W_C$. Controller 50 may then activate an alarm when the total work performed exceeds the $W_C$ level. In some embodiments, due to tolerances of electrical components, controller 50 may adjust $W_T$ and $W_C$ based upon power levels measured during operation of the device. In some embodiments, a temperature sensor may be provided at the inlet of the device to measure the inlet temperature of the gas entering the heater/humidifier 31. The inlet temperature may be used to adjust the values of $W_T$ and $W_C$ to provide proper control.

In order to supply power to the heater 31a either an analog or digital power supply can be used. In this embodiment, controller 50 may control the power delivered to the heater hydrator 31a using pulse-width modulation as discussed above. Suitable microcontrollers for providing pulse-width modulation are commercially available from numerous sources including Microchip Technology, Inc. of Chandler Ariz.

Refill alarm system 20 may include a meter (not explicitly shown) that measures the total work performed by power source 51. Typically, a work meter such as a watt-hour meter can be used to measure the total work if pulse-width modulation is not used. When the total work performed reaches a preset level $W_C$ a signal may be sent to a refill alarm 62 though electrical leads 61. The refill alarm 62 can include a visual alarm 64 such as a light or LED and/or an audible alarm 65 such as a bell or a buzzer. Still other types of devices are useable with the invention including electronic or vibratory devices.

In other embodiments, it is possible to establish a range of instantaneous power that indicates normal operation. As the charge of hydration fluid is exhausted, less power will be required to heat the gas. Thus, it is possible in some embodiments to establish a threshold below which the instantaneous power should not drop over a sustained period of time when insufflation gas is flowing. This method needs to take into account that gas may be flowing rapidly or not at all during a typical surgery. Thus, gas flow should preferably be taken into account when using this method. One could use the flow meter 72 or flow meters within insufflator 32 (or signals therefrom indicating flow) to determine the flow rate of the insufflation gas. One could determine that hydration fluid needs to be recharged by determining whether the instantaneous power drops below a threshold either once or multiple times over a specific time period. Such a threshold could be different for different flow rates or ranges of flow rates.

It should be noted that in some systems, there will be time periods where no power is being supplied to the heater in heater hydrator 31. Controller 50 may be designed such that it does not perform comparisons of power consumption during those time periods. In addition, there will be time periods where little or no insufflation gas is flowing and less power will be needed to maintain the temperature and humidity of the gas within heater/hydrator 31. In an embodiment where the instantaneous power level triggers the alarm, the threshold power level should be chosen to be low enough (or other control exercised such as not making a comparison during no-flow or low-flow conditions) such that no-flow or low-flow conditions do not trigger the alarm.

Figure 2:
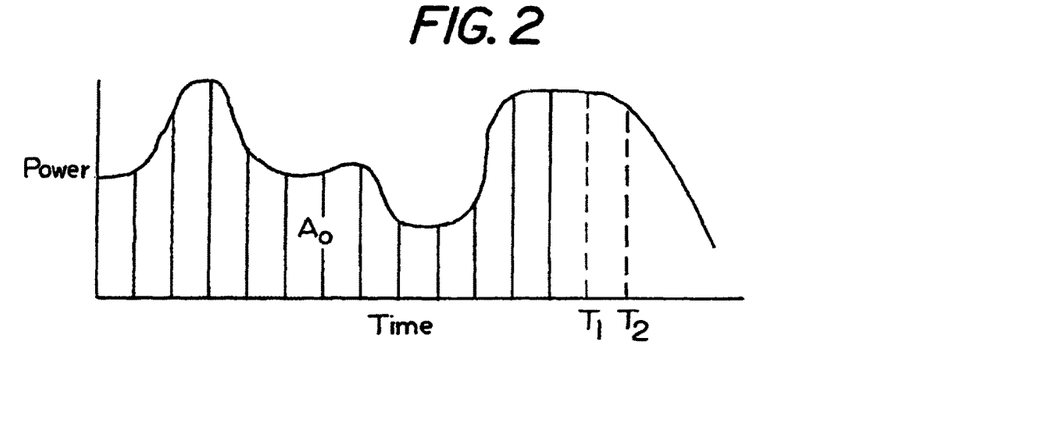
FIG. 2 is an example graph of the power consumed as a function of time during a medical procedure.
Figure 3:
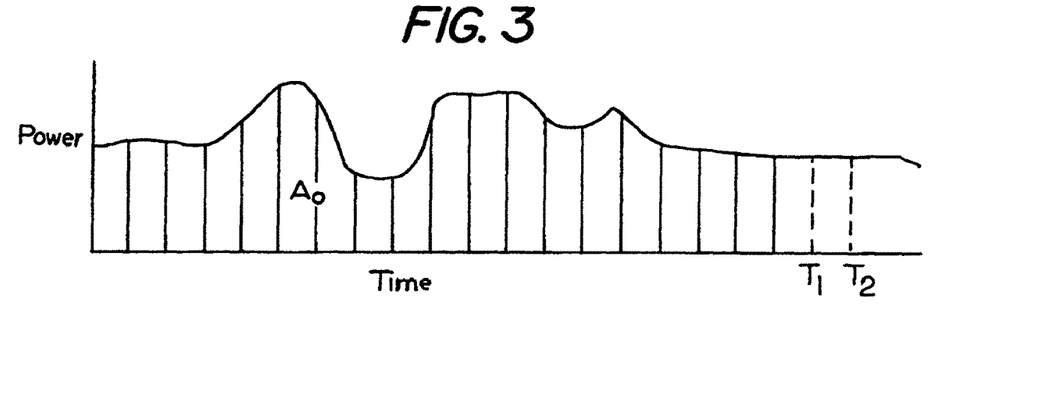
FIG. 3 is an example graph of the power consumed as a function of time during a different medical procedure.

FIG. 2 is a graph illustrating how power may vary verses time during an example laparoscopic surgery. In the graph, the area $A_O$ under the curve represents the total work and the horizontal axis represents the time elapsed. At a time $T_2$ the power needed to heat the insufflation gas and the hydration fluid to the proper conditions state drops off rapidly due to the consumption of the initial charge of hydration fluid in the heater hydrator. FIG. 3 shows a similar graph of power versus time during another example medical procedure. Note that the labels $T_1$ and $T_2$ are unique to each of FIGS. 2-4 and do not represent the same time in the different figures. In other words, these Figures are independent of one another and the use of the same labels does not indicate the same time. The same is true of $A_0$, the area under the curve. This area is different for each of FIGS. 3-4.

Figure 4:
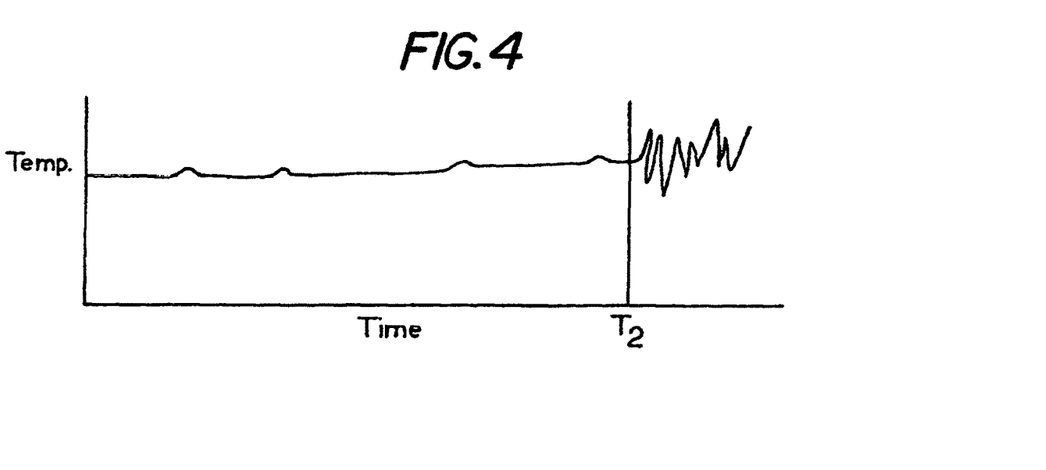
FIG. 4 is an example graph of temperature of the hydration fluid as a function of time.

FIG. 4 shows a graph of a temperature signal of the insufflation gas in the heater hydrator 31 as a function of time as measured by temperature sensor 56. The output generally is constant with minor variation as hydration fluid is consumed in the hydrator. Once hydration fluid in the heater hydrator 31 is totally consumed at time $T_2$, however, the measured temperature may change more erratically in some embodiments. The change in the pattern of the temperature sensor signal can be used to confirm that the hydration fluid in the heater hydrator 31 has been consumed or as indicator that the hydration fluid has been consumed.

The change in temperature signal can be used as a confirmation that the hydration fluid has been consumed in hydrating the insufflation gas. An alarm can be generated when this occurs or the power shut down to the heater or both. Thus, an additional feature of the invention can include the monitoring of the temperature signal of the conditioned gas proximate or inside the heater hydrator and activating an alarm when the temperature signal of the insufflation gas begins to vary significantly as illustrated in FIG. 4.

A reference to system 10 in FIG. 1 shows an optional humidity sensor 70 located in heater hydrator 31 with the humidity sensor 70 sending information on the humidity of the insufflation gas to refill alarm through lead 57 and lead 71. If the output of the humidity sensor 70 decreases below an acceptable level the refill alarm 62 may alert an operator to the low hydration condition through an alarm using either an audio alarm 65 or a visual alarm 64 or both. Humidity sensors sold by Ohmis Instruments Co. of Easton Md. and America Humirel of Chandler Ariz., for example, may be used.

In some embodiments, humidity sensor 70 will be omitted. In some embodiments, multiple humidity sensors will be used in the manner that multiple temperature sensors were used above. In other embodiments, one or more humidity sensors 70 may be used in conjunction with any of the other techniques discussed herein to indicate when a recharge of humidification liquid is desirable. For example, a recharge may not be indicated by an alarm until multiple methods indicate that a recharge is desirable. It should be noted that any of the methods discussed herein can be used to turn off the heater in heater hydrator 31 in addition to or instead of providing an alarm.

The total amount of insufflation gas supplied to the heater hydrator 31 may be proportional to the consumption of hydration fluid. By measuring the total quantity or volume of insufflation gas supplied to the heater hydrator 31 during the heating and hydration process, one can provide an indication of when to replenish the hydration fluid. One can experimentally determine the total volume of insufflation gas supplied to the heater hydrator 31 that exhausts (or substantially exhausts) a predetermined quantity of hydration fluid to obtain a total flow level $Q_T$. Experiments will show a small range of total flow and the minimum value of total flow that substantially exhausts the hydration fluid would preferably be chosen as the value to test against. Once $Q_T$ is known one can then determine a recharge total flow $Q_C$, which is equal or less than the total flow $Q_T$ to use for activating the alarm to alert a person to recharge the heater hydrator 31 before the hydration fluid is consumed. For example, one can select a total gas flow of 0.9 $Q_T$ as a total gas flow where the user should be alerted to recharge the heater/hydrator 31 with fluid. By measuring the total volume of insufflation gas consumed, one can indirectly determine a desirable time to replenish the hydration fluid in the heater hydrator without measuring humidity.

FIG. 1 also shows a sensing system for measuring the total volume of insufflation gas consumed comprising a flow meter 72 that measures the total volume of insufflation gas that flows threrethrough. The total flow of insufflation gas can be monitored by flow meter 72 to send a signal to refill alarm 62 or to controller 50 which may control refill alarm 62. Note that refill alarm 62 may be controlled by controller 50 in any embodiment. For example, once the total flow reaches a level $Q_1$ the refill alarm 62 provides either an audio or visible alarm to alert the operator to recharge the heater hydrator 31. Flow meters for measuring total flow are commercially available from Motorola of Schaumburg Ill. Another commercially available Airflow and Temperature sensor is sold by One Technology of Norwood Mass. There are many possibilities for using one or more of these methods to determine when to recharge a heater hydrator. The measurements of flow of insufflation gas, instantaneous power, temperature, or work in heating and hydrating can be used alone or in combination. If used in combination one can serve as a backup for the other. For example, the flow meter 72 could provide the first indicator of low humidity thereby activating the visible alarm 64 and the power consumed could provide the second alarm alerting the operator by activating the audible alarm. Either method alone could activate either alarm. Also, both might need to indicate a recharge condition before any alarm was activated. Thus the invention includes circuitry responsive to a sensor for determining when a heater humidifier used with a laparoscopic insufflator should be recharged with humidifying liquid in response to a signal from a sensor by providing an alert signal, which can activate an alarm.

Although refill alarm system 20 is shown as separate from insufflator 32, some or all of the circuitry could be a part of insufflator 32. Refill alarm system 20 could be separate control circuitry within insufflator 32 or could be integrated in whole or in part with the control circuitry of insufflator 32. As insufflator 32 typically includes one or more flow meters 72 and keeps track of the total volume of gas consumed, refill alarm system 20 could be provided with electrical signals from a flow meter inside of insufflator 32 or from flow meter 72 through electrical lead 73 that provide the total volume of gas supplied by insufflator 32 during a procedure. While a flow meter is described to measure the volume of gas consumed and provide an electrical signal one could also measure the mass or quantity of gas consumed with a mass meter to provide a signal to the control circuitry.

Figure 5:
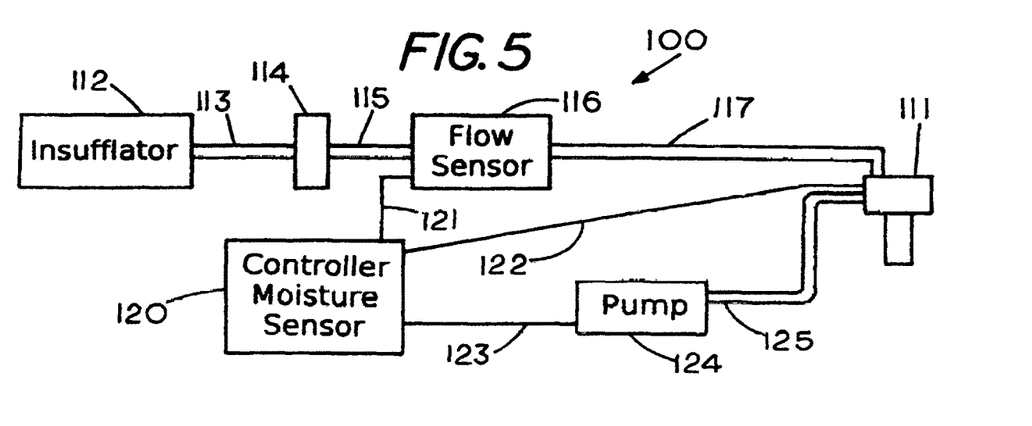
FIG. 5 is a block diagram of a system for on-the-go hydration of a gas conditioning device.
Figure 6:
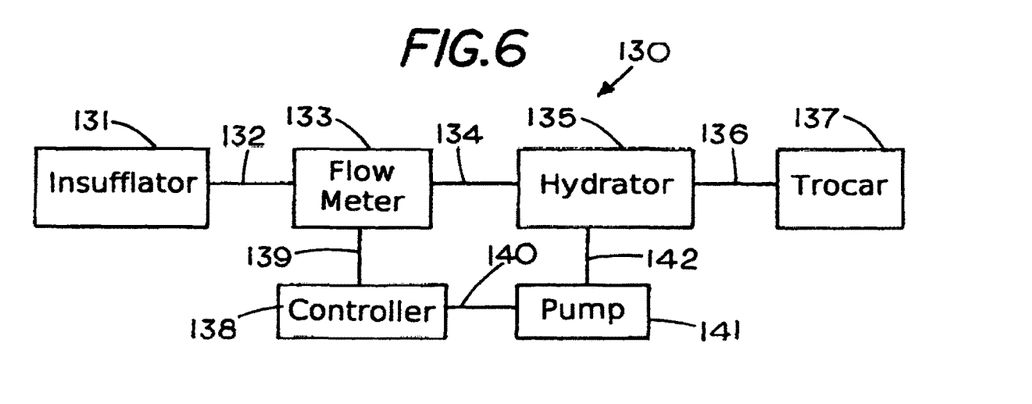
FIG. 6 is a block diagram of a system for on-the-go hydration of a gas conditioning device.

FIG. 5 and FIG. 6 show examples of two types of systems capable of supplying hydration fluid to gas conditioning devices, which have a hydrator for hydrating an unconditioned insufflation gas. The systems may include on-the-go hydration and on-the-go heating of an unconditioned insufflation gas in the gas conditioning device.

FIG. 5 shows an example of a system where the gas conditioning device is located in a trocar 111. In this type of system the trocar contains a hydrator or a hydration chamber for receiving both a hydration fluid and an unconditioned insufflation gas. An insufflation system where the trocar has a hydrator for heating and hydrating an unconditioned insufflation gas is shown in pending U.S. patent application titled GAS CONDITIONING TROCAR, Ser. No. 12/381,978 filed Mar. 18, 2009 and is hereby incorporated by reference.

FIG. 6 shows an example of a system where the hydrator 135 is located outside the trocar 137 with the hydrator receiving insufflation gas from an insufflator 131. An example of such a hydrator is the Insuflow Device®, which is sold by Lexion Medical of St. Paul, Minn. The device is shown and described in Ott et al U.S. Pat. Nos. 5,411,474; 6,068,609 and 7,066,902, which are hereby incorporated by reference.

In either system it may be necessary to replenish the hydration fluid in the hydrator either before or during a medical procedure by injecting additional hydration fluid into the hydrator.

Referring to FIG. 5, the system 100 maintains the conditioning of an insufflation gas during a medical procedure by intermittently replenishing the hydration fluid in the hydrator, which is located in the gas conditioning trocar 111. Typically, the medical procedure is endoscopy and more specifically laparoscopy. The invention may also be used during thoracoscopy as well as other medical procedures. The system 100 may include a heater and hydrator in trocar 111 for heating and hydrating an insufflation gas delivered from an insufflator 112, which supplies an insufflation gas to the heater and hydrator as needed. In some embodiments, the heater and hydrator in the trocar 111 may be replaced by a hydrator alone. Typically, a hydrator contains a hydrophilic media to absorb a liquid hydration fluid to enable the hydration fluid to enter a vapor phase, which causes humidification of the insufflation gas flowing through the hydrator.

In system 100 a source of medical gas may be located in or connected to insufflator 112. The insufflator 112 may contain a flow or pressure regulator or other device to control the delivery of an unconditioned medical gas, such as carbon dioxide, to an insufflation device 111 although the system may be used with other insufflation gasses. The medical insufflation gas may be delivered through a continuous flow of insufflation gas into the inflation device 111 or through repeated pulses of insufflation gas into the inflation device 111. In either case one needs to maintain the pressure in the cavity of the patient to sustain the medical procedure. During the inflation process the insufflation gas flows through a filter 114 which removes unwanted containments from the medical gas and a flow sensor 116, which measures the volumetric flow of medical gas therethrough, as well as through various lengths of flexible tubing 113, 115 and 117 that are connected between the various components of the system 100 to thereby provide a closed fluid path between the medical gas in insufflator 112 and the inflation device such as a trocar 111, which extends at least partially into a body cavity of a patient.

System 100 includes a hydrator or gas conditioning chamber, which is located in the inflation device 111, with the hydrator having a liquid absorbing member, such as a hydrophilic member, for receiving and holding a hydration fluid proximate the insufflation gas to enable humidification of the insufflation gas during its presence proximate the hydration fluid. In some instance a heating element may be present in the gas conditioning chamber so the insufflation gas can be both heated and hydrated while in the gas conditioning chamber.

System 100 may also include a controller or microprocessor 120, which connects to a flow sensor 116 through an electrical lead 121, with the controller 120 responsive to flow conditions in flow sensor 116 to enable the controller 120 to recognize the presence or absence of the flow of medical insufflation gas into the insufflation device 111. Flow sensor 116 may be a flow meter or any other type of device that can determine if an insufflation gas is flowing therethrough. An electrical lead 122 connects controller 120 to a moisture sensor (not shown), which is located in the trocar 111. The moisture sensor measures the conditioning level of the insufflation gas in the trocar 111. If the conditioning level of the insufflation gas is below an acceptable level the controller 122 can be readied for the process of supplying hydration fluid to the hydration chamber in trocar 111. An electrical lead 123 connects controller to a pump 124, which contains a source of hydration fluid or is connected to a source of hydration fluid that can be delivered to the hydrator. A conduit 125 for delivery of the hydration fluid from pump 141 to trocar 111 connects the output of pump 124 to a hydrator located in a hydration chamber in trocar 111. While a moisture sensor may be used to measure the conditioning level of the insufflation gas in some cases the moisture sensor may be eliminated.

In operation of the system shown in FIG. 5 flow sensor 116 measures the volumetric flow of medical insufflation gas flowing through line 117 while a moisture sensor in a gas conditioning trocar 111 determines whether the moisture content of the insufflation gas is sufficient. Both the flow and the moisture content of the insufflation gas may be monitored by controller 120. If the controller 120 determines an absence of insufflation gas flowing through flow sensor 116 and the moisture content of the insufflation gas is insufficient or below a predetermined level the controller 120 activates pump 124 which pumps liquid hydration fluid into a hydration chamber in trocar 111. If the flow sensor determines that insufflation gas is flowing into trocar 111, the controller 120 stops pump 124 to prevent pumping liquid hydration fluid into the hydration chamber in trocar 111, thus avoiding a condition where liquid hydration fluid may be forced through trocar 111 before the liquid hydration fluid has had time to be absorbed by the hydration chamber media, such as a hydrophilic media in the hydration chamber of the trocar.

The controller 120, which can terminate the administration of liquid hydration fluid into the hydration chamber of trocar 111 when insufflation gas flow is present, can also be used in an alternate mode to allow simultaneous flow of liquid hydration fluid and insufflation gas under certain determinable conditions described herein.

During a simultaneous flow of hydration fluid and insufflation gas from the insufflator, the controller 120 can automatically terminate, or limit, the delivery of the liquid hydration fluid to the hydration chamber before the liquid hydration fluid flows directly through the hydration chamber of trocar 111.

Depending on various factors, which are generally unique to an insufflation device, the liquid hydration fluid can be safely injected into the hydration chamber of trocar 111 as insufflation gas flows through the hydration chamber, if one avoids undesirable encapsulation or entrainment of the liquid hydration fluid droplets in the insufflation gas (i.e. the fluid remains in a liquid state in the stream of insufflation gas). Such an on-the-go system for simultaneous injection of liquid hydration fluid and insufflation gas is useful where it is anticipated that the flow of insufflation gas is substantially continuous with only limited interruptions.

The medical insufflation gas flow condition where the hydration chamber can be hydrated on-the-go is generally specific to the type of insufflator and the type of hydration fluid, however, the personnel operating the insufflator can perform a preoperative field test to readily determine critical conditions typically, i.e. conditions such as the volume and flow rate of the hydration fluid where the liquid droplets of hydration fluid flow directly into a patient's body cavity. For example, prior to initiating a medical procedure a medical professional turns on the insufflation gas and at the same time injects hydration fluid at an ever-increasing rate into the hydration chamber of trocar 111. When the person observes that the liquid hydration fluid flows through the hydration chamber of trocar 111 without being absorbed by the hydration chamber media, the person notes the critical flow condition that causes the liquid hydration fluid to be carried through trocar 111 without being fully absorbed by the hydration chamber media. The operator then sets the controller to automatically limit or cease injection of hydration fluid prior to the occurrence of the critical flow condition.

Thus, a feature of the invention is coupling the delivery of liquid hydration fluid to a condition where there is no flow of medical insufflation gas, which allows one to supply liquid hydration fluid to the hydration chamber of trocar 111 without accidentally forcing liquid hydration fluid through the hydration chamber before the liquid hydration fluid can be absorbed by the hydration chamber media.

A further feature of the invention is that the controller 120 can be set to automatically initiate and terminate the delivery of the liquid hydration fluid to the hydration chamber during simultaneous flow of medical insufflation gas and the liquid hydration fluid into the hydration chamber if the flow of medical insufflation gas is such that the liquid hydration fluid can not be readily absorbed by the hydration chamber media. The critical conditions for setting the controller can be determined by an on-the-go field test by the medical personnel. Additionally, worst case conditions may be preset into controller 120 by the manufacturer, taking into account worst case flow conditions involving the most widely used and accepted insufflators currently available.

Thus the controller 120 can be set to automatically initiate and terminate the delivery of the liquid hydration fluid to the hydration chamber of trocar 111 during a condition of no flow of insufflation gas into the hydrator or during a flow of insufflation gas. In either case controller 120 can prevent liquid hydration fluid from flowing directly through the trocar in the form of liquid droplets or the like.

An example of a suitable type of hydration pump for intermitting supplying hydration fluid is a servo driven syringe pump although other means or pumps may be used for delivery of the hydration fluid during time specified intervals including peristaltic pumps, pressure cuffs, screw driven syringe pumps and other means that can periodically deliver small volumes of hydration fluid. With use of a servo driven syringe pump an initial volume of hydration fluid is introduced into the syringe pump 124, which is connected to the controller or microprocessor 120, which determines when the hydration fluid in the pump 124 should be injected into the hydrator 111.

The flow sensor or flow meter 116 indicates when the insufflation gas is in a flow condition or a no flow condition in conduit 117. In response to a no flow condition and in some cases other threshold conditions the controller or microprocessor 120 activates the hydration pump 124 to deliver hydration fluid to the hydration chamber in trocar 111. In order to avoid over supplying of hydration fluid to the hydration chamber controller 120 can be set to only activate the pump 124 when additional system threshold conditions are met. For example, the total system volume of insufflation gas that is supplied to the insufflation device 111 after initiating of the surgical procedure may be a threshold condition. That is, the controller 120 may not activate pump 124 until a minimum amount of insufflation gas has been consumed. This type of threshold condition depends on the volumetric capacity of the hydration chamber in the insufflation device to hold an initial charge of hydration fluid, which is sufficient to humidify a predetermined volume of dry insufflation gas. For example, a hydrator may have a hydration chamber that has the capacity to contain sufficient liquid hydration fluid to hydrate only 150 liters of an insufflation gas, consequently, before the 150 liters of insufflation gas have been consumed additional hydration fluid needs to be supplied to the hydration chamber in order to replenish the hydration fluid for continuing the hydration of the insufflation gas. Thus a threshold condition may be based on the amount or volume of insufflation gas that has been consumed during the insufflation process. For example, one may want to initiate the supply of hydration fluid to the hydrator after half of the determined amounts of insufflation gas has been consumed.

Another threshold condition where the controller may be prevented from activating the pump may be based on elapsed time. Sill another threshold condition may be relative humidity of the insufflation gas, for example if the hydrator 111 includes a humidity sensor the controller 120 may be programmed to not activate the pump 124 until the humidity of the insufflation gas falls below 100% relative humidity or a predetermined conditioning level. Other threshold conditions may be included based on the needs of the system. Thus, a benefit of the existing system is that the liquid hydration fluid can be supplied to the hydration chamber of the trocar under a variety of conditions without concern for injecting too little or too much hydration fluid into the system. That is the liquid hydration fluid can be supplied before the medical procedure begins, during the medical procedure or on-the-go with the delivery of hydration fluid automatically limited to those time periods when the delivery of the insufflation gas does not adversely affect the operation of the system or would harm the patient.

A further benefit of the hydration system 100 is that it avoids human errors, which may be caused by a failure of the medical staff to notice that the liquid hydration fluid in the hydration chamber has been depleted. In addition, since the system can hydrate the insufflation gas without the assistance of any medical staff it frees the medical staff to attend to other critical matters during the medical procedure.

A further benefit of the hydration system 100 is that during an on going medical procedure it eliminates supplying liquid hydration fluid to the hydration chamber in the trocar 111 during times which may be inconvenient for the medical staff. It should be pointed out that while various factors or threshold conditions have been identified to protect the system 100 from introducing excess hydration fluid into the hydration chamber in trocar 111 still other conditions may be monitored to further limit the times when one can supply hydration fluid to the hydration chamber in trocar 111 without departing from the spirit and scope of the invention.

FIG. 6 is a block diagram of another system 130 for on-the-go hydration of an insufflation gas. In this example the system 130 includes an insufflator 131 having a source of medical insufflation gas 131, a flow meter 133, a hydrator 135, which is separate from a trocar 137, a controller or microprocessor 138 and a pump 141. During the operation of the system 130 the insufflation gas emanating from insufflator 131 flows through a conduit 132 and through flow meter 133. The insufflation gas then flows through a conduit 134 into a hydrator 135 where the insufflation gas is hydrated. The hydrated insufflation gas then flows into trocar 137 through conduit 136. In this example, in contrast to the system of FIG. 5, the hydrator 135 is separate from the trocar 137. The flow of insufflation gas into a hydration chamber (not shown) in hydrator 135 may depend on various factors including the downstream pressure of the insufflation gas in the body cavity with the flow of insufflation gas controlled by a flow regulator in the insufflator 131 or through a feed back system that includes a pressure sensor in the trocar to monitor the actual gas pressure in the patient's body cavity. For example, if the insufflation gas pressure in the patient's body cavity is within a prescribed range no fresh insufflation gas flows into the hydrator 135 on the other hand if the insufflation gas pressure in the patient's body cavity is to low the insufflation gas flows into the hydrator 135 from the source of medical gas in insufflator 131. The presence of a flow condition or a no flow condition of the insufflation gas can be sensed by the controller 138. Once controller 138 determines the insufflation gas is in a no flow condition the controller 138 can activate pump 141 which delivers the hydration fluid to the hydrator 135 until such time as the insufflation gas in the hydrator 135 is hydrated, the insufflation gas begins to flow into the hydrator, or some other condition when hydration would not be beneficial. While the system has been described as capable of injecting hydration fluid when the insufflation gas is in a no flow condition in some cases the insufflation gas may be introduced under low flow conditions, that is a conditions where the flow of insufflation gas is so low that the hydration fluid can be timely absorbed in the hydration chamber without passing directly through the hydrator 135.

While the systems described herein are capable of on-the-go delivery of hydration fluid to a hydrator during a medical procedure the systems may also be used to supply hydration fluid to a hydrator during a non on-the-go condition, for example prior to initiating a medical procedure that requires insufflation of a body cavity or during pauses in the surgical procedure.

Figure 7:
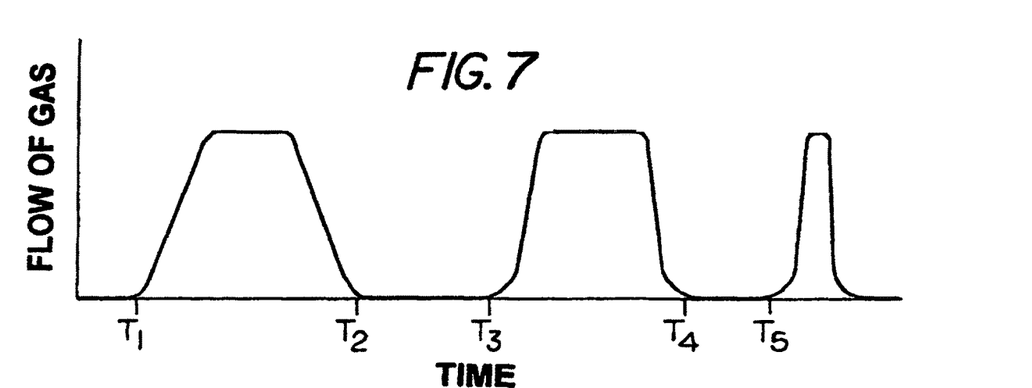
FIG. 7 is graph of the flow of insufflation gas into a hydrator as a function of time.

To illustrate the limited and timely delivery of hydration fluid to a hydrator where there is no flow of insufflation gas reference should be made to FIG. 7, which shows a graph of the flow of an insufflation gas from insufflator 131 into hydrator 135 as a function of time. The graph shows that during the initial period $T_1$ no insufflation gas is supplied to hydrator 135. Starting at time $T_1$, a pulse of insufflation gas flows into the hydrator 135 until time $T_2$ at which time the insufflation gas ceases to flow until time $T_3$ when another pulse of insufflation gas is injected into the system with the insufflation gas ceasing to flow after the time $T_4$. It is during the time period between $T_2$ and $T_3$ and the time period between $T_4$ and $T_5$ i.e. where the insufflation gas is not flowing, that the controller 138 that one can safely inject hydration fluid into the hydrator 135 without accidentally forcing the liquid hydration fluid through the hydrator 135 and into the gas line 136 before the liquid hydration fluid can be vaporized and absorbed by the insufflation gas. Thus a feature of the invention is that controller 138 or controller 120 can initiate and terminate the delivery of the liquid hydration fluid to the hydrator during time intervals of no flow of medical insufflation gas into the hydrator to prevent or inhibit accidentally forcing the liquid hydration through the hydrator. Thus, as illustrated in FIG. 7 a pump 124 or 141 can deliver charges or pulses of liquid hydration fluid between pulses or charges of the insufflation gas. The pulses may be of varying duration and or varying intensity depending on the hydration system as well as the need for hydration of the insufflation gas. In some cases the termination of the delivery of liquid hydration fluid may be based on a maximum time period and in other cases the delivery of liquid hydration fluid may terminate upon the sensor determining that the liquid hydration fluid being delivered to the hydrator is not being absorbed by the hydrator.

In still other methods the deliver of liquid hydration fluid to the hydrator 135 may be directly coupled to the delivery of insufflating gas to the inflation device. Thus, when the system 100 or 130 is supplying insufflation gas to the hydrator, for example, between the times $T_1$ and $T_5$ the controller 138 or 120 prevents delivery of liquid hydration fluid to the hydrator by incapacitating the pump 124 or 141. In this example the controller 120 or 138 may be responsive to the activity of the insufflator 112 or 131 rather than a conditioning level down stream of the insufflator. In this case the supplying of liquid hydration fluid is coupled to the activity of the insufflator. To avoid over hydration of the hydrator one may limit the liquid hydration fluid supplied based on the amount of insufflation gas supplied to the inflation device.

In some cases one may simultaneously supply a pulse or charge of insufflation gas to the hydrator and a pulse or charge of hydration fluid to the hydrator with the pulse or charge of hydration fluid supplied to the hydrator during a period when the pulse or charge of insufflation gas is insufficient to force the hydration fluid through a hydration member. In other cases one may couple the pulse or charge of hydration fluid into the hydrator to the absence of a pulse or charge of medical insufflation gas flowing into the hydrator so that liquid hydration fluid flows into the hydrator only when no insufflation gas flows into the hydrator.

Thus method may include powering a hydration fluid pump 141, 124 during a period when the flow of insufflation gas is insufficient to force the liquid hydration fluid through a hydration member before the liquid hydration fluid can be absorbed by the hydration member by coupling the flow of liquid hydration fluid into the hydrator to the absence of a pulse of medical insufflation gas into the hydrator. It will be apparent that other methods and apparatus may be employed to limit the delivery of liquid hydration fluid without departing from the spirit and scope of the invention described herein. For example, the controller may intermittently deliver liquid hydration fluid to the hydrator in response an absence of a flow of insufflation gas.

As described herein one feature of the invention is a method of automatically hydrating an insufflation gas during a medical procedure without forcing liquid hydration fluid through a trocar and into a patient by supplying a medical insufflation gas to the hydrator, monitoring the flow of medical insufflation gas to the hydrator; and supplying the liquid hydration fluid to the hydrator during a time period where there is an absence of medical insufflation gas flowing into the trocar to thereby rehydrate the hydrator without accidentally forcing liquid hydration fluid through the trocar. By doing so one can deliver the medical insufflation gas containing hydration fluid in vapor form within the insufflation gas.

Another feature of the invention is that a medical gas conditioning system comprising, a hydrator, a source of medical insufflation gas, a source of hydration fluid and a controller responsive to a hydration condition in the hydrator can determine when to initiate delivery of a hydration fluid to the hydrator and when to suspend delivery of the liquid hydration fluid to thereby avoid directing liquid hydration fluid through the hydrator before it can be absorbed into the insufflation gas.

We claim:

1. A method of automatically hydrating a medical insufflation gas during a medical procedure comprising: measuring a volume flow of the medical insufflation gas through a flow meter; sending a signal from the flow meter to a controller in response to the volume flow of the medical insufflation gas through the flow meter; activating an electrically powered hydration fluid pump in response to the signal from the controller that is in electrical communication with the electrically powered hydration fluid pump; and determining a first condition when there is no flow of the volume flow of the medical insufflation gas or a second condition when the volume flow of the medical insufflation gas to a hydrator is sufficiently slow so that a liquid hydration fluid is absorbed by the medical insufflation gas which is determined through an observing of the volume flow of the medical insufflation gas through the hydrator; and pumping liquid hydration fluid into hydrator during the first condition or the second condition to hydrate the medical insufflation gas while allowing the liquid hydration fluid to be absorbed by the medical insufflation gas therein without forcing the liquid hydration fluid through the hydrator.

2. The method of claim 1, including a step of directing the medical insufflation gas into a trocar.

3. The method of claim 1, wherein in response to a first signal from the controller the liquid hydration fluid is pumped into the hydrator while the medical insufflation gas does not flow into the hydrator.

4. The method of claim 1 wherein controller in response to a mass flow determines when to pump the liquid hydration fluid into the hydrator as the medical insufflation gas flows through the hydrator.

5. The method of claim 1 wherein the controller directs a pulse of liquid hydration fluid into the hydrator.

6. The method of claim 1 wherein in response to a second signal from the controller the liquid hydration fluid is pumped into the hydrator as the medical insufflation gas flows in the hydrator.

7. The method of claim 6 wherein in response to a third signal from the controller the liquid hydration fluid is pumped into the hydrator while the medical insufflation gas flows into the hydrator during a period when the volume flow of the medical insufflation gas flowing through the hydrator is insufficient to force the liquid hydration fluid through a hydration member.

8. The method of claim 7 wherein the hydrator is located in a trocar when the liquid hydration fluid is delivered to the hydrator in response to the first, second or third signal from the controller.

\* \* \* \* \*